United States Patent
Balcombe et al.

(10) Patent No.: US 9,125,824 B1
(45) Date of Patent: Sep. 8, 2015

(54) METHODS AND SYSTEMS FOR PROCESSING ORGANIC TRANS-RESVERATROL AS DIETARY SUPPLEMENTS

(75) Inventors: Naomi Balcombe, Gainesville, FL (US); Robert Maru, Livingston, NJ (US); Surendra Vallabhaneni, Flemington, NJ (US)

(73) Assignee: InnoVitamin Organics, LLC, Boca Raton, FL (US)

( * ) Notice: Subject to any disclaimer, the term of this patent is extended or adjusted under 35 U.S.C. 154(b) by 666 days.

(21) Appl. No.: 13/173,927

(22) Filed: Jun. 30, 2011

Related U.S. Application Data

(60) Provisional application No. 61/390,366, filed on Oct. 6, 2010.

(51) Int. Cl.
*A61K 9/14* (2006.01)
*A61K 9/20* (2006.01)
*A61K 9/16* (2006.01)

(52) U.S. Cl.
CPC ............. *A61K 9/2054* (2013.01); *A61K 9/1682* (2013.01)

(58) Field of Classification Search
CPC ..... A61K 9/16; A61K 9/1682; A61K 9/1688; A61K 9/1694; A61K 9/2077; A61K 9/2054
USPC ........... 424/400, 489, 490; 426/443, 478–481
See application file for complete search history.

(56) References Cited

U.S. PATENT DOCUMENTS

| | | | |
|---|---|---|---|
| 6,190,716 B1 * | 2/2001 | Galbreath, Jr. | 426/443 |
| 2005/0043274 A1 * | 2/2005 | Murad | 514/62 |
| 2008/0260935 A1 * | 10/2008 | Alkayali | 426/648 |
| 2009/0163580 A1 * | 6/2009 | Yatcilla et al. | 514/456 |

OTHER PUBLICATIONS

Reserveage Organics, retrieved from http://www.reserveage.com; retrieved on Jun. 30, 2011.
ResVitale, The Purest Youth Activating Collagen Enhance, 1 pg.; retrieved on Jun. 30, 2011.
Vine to Capsule, Trademark Application, 1 pg.; Filed Jul. 24, 2009.

* cited by examiner

*Primary Examiner* — Michael G Hartley
*Assistant Examiner* — Micah-Paul Young
(74) *Attorney, Agent, or Firm* — Brian S. Steinberger; Law Offices of Brian S. Steinberger, P.A.

(57) ABSTRACT

Methods and systems for processing organic trans-resveratrol for use in dietary supplements is disclosed. The process begins with harvesting grapes, stems and leaves, placing them in a cloth sack and delivering the grapes, stems and leaves to a nearby processing facility within less than 25 minutes. Thereafter, grapes are pressed to extract the juice and the residual pomace of skin, seeds and stems is removed from the pressing cylinder, ground to a fine mesh powder (approximately 50 mesh size), mixed with a bioflavanoid compound and *polygonum cuspidatum*, handled in controlled temperatures between approximately 10.0° C. (50 degrees F.) to approximately 30° C. (86 degrees F.) and with humidity of the storage area at less than 35%. The process results in a high quality and high quantity yield of a stable, organic trans-resveratrol for use in dietary supplements that are bioavailable and easily absorbed by the consumer of the dietary supplement.

12 Claims, 2 Drawing Sheets

METHODS AND SYSTEMS FOR PROCESSING ORGANIC TRANS-RESVERATROL AS DIETARY SUPPLEMENTS

This invention claims the benefit of priority to U.S. Provisional Patent Application Ser. No. 61/390,366 filed Oct. 6, 2010.1

FIELD OF INVENTION

The present invention relates generally to the processing of trans-resveratrol and more specifically to a method and system for processing organic trans-resveratrol and the production of dietary supplements there from.

BACKGROUND AND PRIOR ART

Resveratrol is a phytochemical that has many health benefits for mammals. Extensive studies have been performed on the mechanism of action and benefits of resveratrol to the consumer. There have also been extensive studies into the advantage of mammals consuming organic and naturally grown products, such as resveratrol. Organic products are grown free of pesticides and allowed to mature naturally. Studies have shown how this natural process boosts the plants own natural defense mechanisms against invading fungus, bugs, and bacteria. These phytochemicals have natural health benefits that translate to consumer of the phytochemicals, as reported by R. Liew in "Cardioprotective and Antiarrhythmic Effects of Resveratrol—a Modern Perspective on an Old Treatment," *Cardiovascular Drugs and Therapy*, January 2009, Vol. 22, No. 6: 427-428.

Resveratrol is one such compound that is produced by grapes other fruits, nuts, and plants, such as *polygonum cuspidatum*, to defend the plant against invaders. Resveratrol has been shown to exist in two isomers, cis and trans. The trans structure of resveratrol has been shown to be an active anti-inflammatory and antioxidant that helps cells regulate internal harmful mechanisms according to G. Kaur et al. in "Effect of wine phenolics on cytokine-induced C-reactive protein expression," *Journal of Thrombosis and Haemostasis*, July 2007, Vol. 5, No. 6: 1309-1317.

Trans-resveratrol is a sensitive molecule that degrades when exposed to light and heat. The trans structure of the molecule will degrade to a cis structure if it is exposed to UV light and temperatures above 110° F. according to *Se Pu* (Chinese Journal of Chromatography) 2004 November; 22 (6) 583-588. The trans structure of resveratrol has numerous health advantages in mammals that include antioxidant and anti-inflammatory protection for cells as reported by Trela, et al. in *J. Argic. Food Chem.* (1996) 44:1253-1257.

When growing, harvesting and processing grapes under strict guidelines, the amount of trans-resveratrol found in grapes can be increased resulting in an increase in the amount of trans-resveratrol in the final product. Improvements in the manufacturing process have also been made to enhance stability and absorption of the trans-resveratrol isomer.

Cis-resveratrol has minimal anti-inflammatory and antioxidant activity which makes it inferior to trans-resveratrol in providing health benefits according to J. Pirkip et al. in "Resveratrol and its gylcon piceid are stable polyphenols," *J. Medicinal Food* 9 (1) 2006, 11-14.

It has also been shown that organic molecules increase the health of mammals consuming them over non-organic and processed foods according to R. F. Edlich, et al. in "Revolutionary advances in organic foods," *Internal and Emergency Medicine*, (2007), 2:182.

Thus, it has become an important focus in science and medicine to include organic molecules such as trans-resveratrol in the diet of man and animals in the form of dietary supplements.

Formulation, development and marketing of dietary supplements are flourishing commercial endeavors today. There remains great demand for high quality, effective dietary supplements. The current invention provides a very high quality dietary supplement containing a complex of trans-resveratrol derived from *polygonum cospidatum*, organic grape skins, vines and seeds. The present invention maximizes the absorption of trans-resveratrol and increases the bioavailability of trans-resveratrol, and other naturally occurring polyphenols such as catechin, epicatechin and OPCs (oligomeric proanthocyanidins), to the consumer of the dietary supplement.

SUMMARY OF THE INVENTION

A first objective of the present invention is to maximize the content of trans-resveratrol harvested from organic grapes and processed for consumption by mammals.

A second objective of the present invention is to use manufacturing procedures which allow for greater absorption of trans-resveratrol when combined with bioflavanoid compounds.

A third objective of the present invention is to use manufacturing procedures that increase the stability of the trans-resveratrol isomer through the entire processing phase.

The fourth objective of the present invention is to increase trans-resveratrol isomer yield which maximizes the total health benefit provided by the dietary supplement prepared therefrom.

The fifth objective of the present invention is to use specialized storage containers which limit UV light exposure and maintain the humidity range within certain levels to provide and enhance stable trans-resveratrol isomer yields.

A method for processing trans-resveratrol for use in dietary supplements can include the steps of harvesting organically grown grapes, vines and leaves, placing the harvested grapes, vines and leaves in a cloth sack, transporting the grapes and vines to a separating facility in a time period between approximately 4 minutes to approximately 25 minutes after harvesting, separating grapes from vines and leaves, putting grapes into wooden cylinder for pressing until a pomace of grape skin, grape seeds and grape stems is left in the cylinder, removing the pomace from the cylinder, adding vines and leaves to pomace, shipping pomace to extraction facility with vines and leaves, storing pomace, vines and leave in an extraction facility, grinding pomace, vines and leaves into a fine powder, shipping fine powder to manufacturing facility, mixing fine powder with bioflavanoid nutrients, storing the mixture of bioflavanoid and fine powder in a vacuum sealed UV light protected container, shipping vacuum sealed container of bioflavanoid and fine powder to manufacturing facility, preparing a dietary supplement product in the form of at least one of capsules, liquids and tablets from the bioflavanoid and fine powder mixture, placing prepared capsules, liquids and tablets in dark container, and shipping dark containers to final destination.

The organically grown grapes and vines can be selected from French Muscadine grapes, American Muscadine grapes and mixtures thereof.

The transporting to a separating facility can be in a time period of from approximately five minutes to approximately ten minutes of harvesting. The pomace of grape skin, grape seeds and grape stems can be mixed with vines and stems and ground to a fine powder, wherein the powder has a mesh size in a range between approximately 40 mesh to approximately 80 mesh.

The fine powder can be mixed with a bioflavanoid selected from at least one of quercetin dihydrate, hesperidin complex, and rose hips concentrate.

The bioflavanoid compound can be quercetin dihydrate.

The controlled environment for storage of the fine powder and bioflavanoid mixture can include a temperature range of between 10.0° C. (50 degrees F.) to approximately 30° C. (86 degrees F.) and a humidity level in the storage area of less than 35% water vapor in the air.

The fine powder and bioflavanoid mixture can be further processed in a granulator that protects the mixture from heat, humidity and UV light in atmospheric conditions.

The granulated fine powder and bioflavanoid mixture can be dried at approximately 26.6° C. (80° F.) to reduce the moisture content of the mixture to a range between 0.1 weight % to approximately 10 wt. %.

The granulated fine powder and bioflavanoid mixture can further include an effective amount of *polygonum cuspidatum* to increase the health benefit provided by the dietary supplement product.

The moisture content of the granulated mixture can be approximately 1% by weight. The method can further include the step of preparing dietary supplements in the form of at least one of capsules, liquids and tablets. The capsules, liquids and tablets can be stored in dark containers for shipment.

A system for processing trans-resveratrol for use in preparation of dietary supplements can include a harvester for organically grown grapes, vines and leaves, a cloth sack for collecting the harvested grapes, vines and leaves, a transporter for transporting the harvested grapes and vines to a separating facility in a time period between approximately 4 minutes to approximately 25 minutes after harvesting, a separator of grapes from vines and leaves; wherein grapes are for pressing and vines and leaves are placed in a storage area, a wooden cylinder for pressing grapes until a solid pomace of grape skins, grape seeds and grape stems is left in the cylinder, a means for removing the pomace from the cylinder, a first mixer for mixing the pomace with vines and leaves, a controlled environment storage area for storing pomace, vines and leaves in an extraction facility, a grinder for grinding pomace, vines and leaves into a fine powder, a second mixer for mixing fine powder with bioflavanoid nutrients, a vacuum sealed UV light protected container for storing the mixture of bioflavanoid and fine powder, a manufacturing facility for preparing dietary supplement capsules, liquids and tablets from the bioflavanoid and fine powder mixture, and a dark container to hold prepared capsules, liquids and tablets of dietary supplements.

The organically grown grapes and vines can be selected from French Muscadine grapes, American Muscadine grapes and mixtures thereof.

The pomace of grape skin, grape seeds and grape stems can be mixed with vines and stems and ground to a fine powder, wherein the powder has a mesh size in a range between approximately 40 mesh to approximately 80 mesh.

The fine powder can be mixed with a bioflavanoid selected from at least one of quercetin dihydrate, hesperidin complex, and rose hips concentrate. The bioflavanoid compound can be quercetin dehydrate.

The controlled environment for storage of the fine powder and bioflavanoid mixture can include a temperature range of between 10.0° C. (50 degrees F.) to approximately 30° C. (86 degrees F.) and a humidity level in the storage area of less than 35% water vapor in the air.

The fine powder and bioflavanoid mixture can be further processed in a granulator that protects the mixture from heat, humidity and UV light in atmospheric conditions.

The granulated fine powder and bioflavanoid mixture can be dried at approximately 26.6° C. (80° F.) to reduce the moisture content of the mixture to a range between 0.1 weight % to approximately 10 wt. %. The moisture content of the granulated mixture can be approximately 1% by weight.

The system can further include preparing dietary supplements in the form of at least one of capsules, liquids and tablets. The capsules, liquids and tablets can be stored in dark containers for shipment.

Further objects and advantages of this invention will be apparent from the following detailed description of a presently preferred embodiment, which is illustrated in the accompanying figure.

DESCRIPTION OF THE PREFERRED EMBODIMENT

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

It would be useful to discuss the meanings of some words used herein and their applications before discussing the method and system of the present invention.

"Organic" is used herein to mean products that are grown free of pesticides and herbicides and allowed to mature naturally.

"*Polygonum cuspidatum*" is also known as Japanese Knotweed and is a large, herbaceous perennial plant, native to eastern Asia in Japan, China and Korea. In North America and Europe the species is very successful and has been classified as an invasive species or weed in several countries.

"Pomace" is used herein to mean grape pomace, the solid material including seeds and skins left over after grapes have been pressed to remove the juice as processed in wineries.

"Vine to Capsule" is a trademarked phrase to represent the technology disclosed by the present invention.

For the first time it is possible to produce a high yield of organic trans-resveratrol and to prepare dietary supplements with both a high quantity and high quality of organic trans-resveratrol using the process of the present invention.

While this concept is a relatively simple one, there are a variety of issues that complicate implementation.

Figure 1:
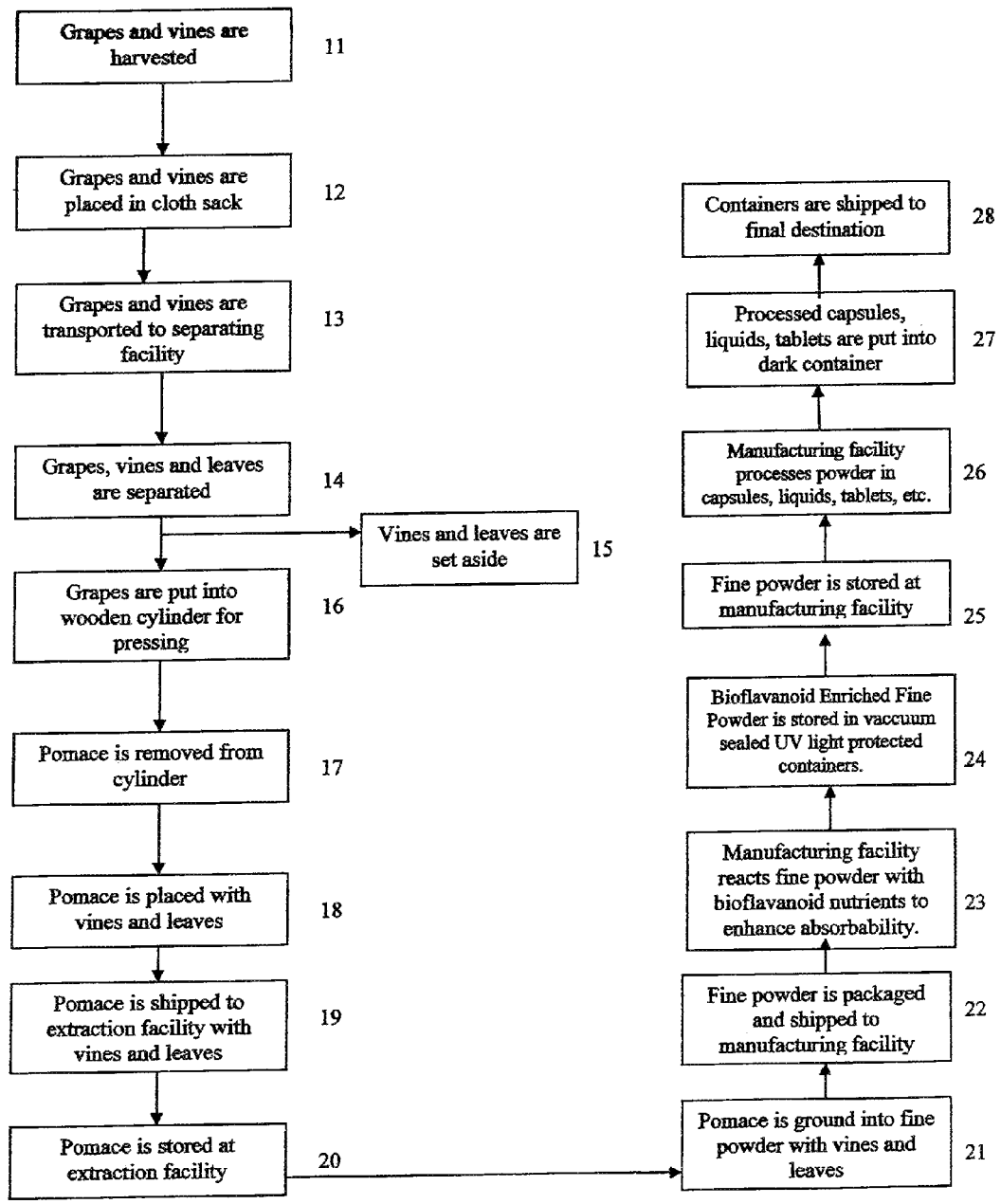
FIG. 1 is a diagram of a method and system for processing trans-resveratrol and the preparation of a dietary supplement therefrom.

Organically grown grapes are harvested, packaged, shipped and processed under strict guidelines to maintain optimum amounts of organic trans-resveratrol. The grapes are grown in fertile soil without addition of any pesticides or herbicides to protect the grape skin, vines, and seeds from invaders. As shown in FIG. 1, when the grape is ready for harvesting, a straight tip pruning sheer is used to split or separate the cluster of grapes from the vine 11. The grapes are placed in a carrying container 12 made of cloth that protects the grapes from UV sunlight and moved to a truck for transport. The grape skins, with vines and seeds are transported 13 to a processing center or facility maintained within approximately 5 minutes from the harvest site or vineyard.

At the processing facility the grape skin, vines and seeds are separated 14. The vines and leaves 15 are separated and stored for other uses. The grapes are placed into a cylinder 16 and pressed. Pressing consists of subjecting the grapes to compression at high pressures to extract the grape juice which is subsequently used as a grape extract. The material left in the cylinder from the pressing of the grapes is a pomace of seeds, flesh and skin. The pomace is removed 17 from the cylinder and stored with the vines and leaves 18. This material is then packaged and taken to the extraction facility 19.

At the extraction facility the pomace is stored 20 in a cool, dark, dry location before grinding into a fine powder. The grinding process uses a blade that rotates at high speeds for a short length of time; this reduces the pomace to a fine powder 21. The fine powder is transferred into a UV protected polyurethane container to ensure moisture and humidity control. The material is shipped to the manufacturing facility 22. The manufacturing facility uses a unique granulation process which protects the material from atmospheric conditions 23.

Figure 2:
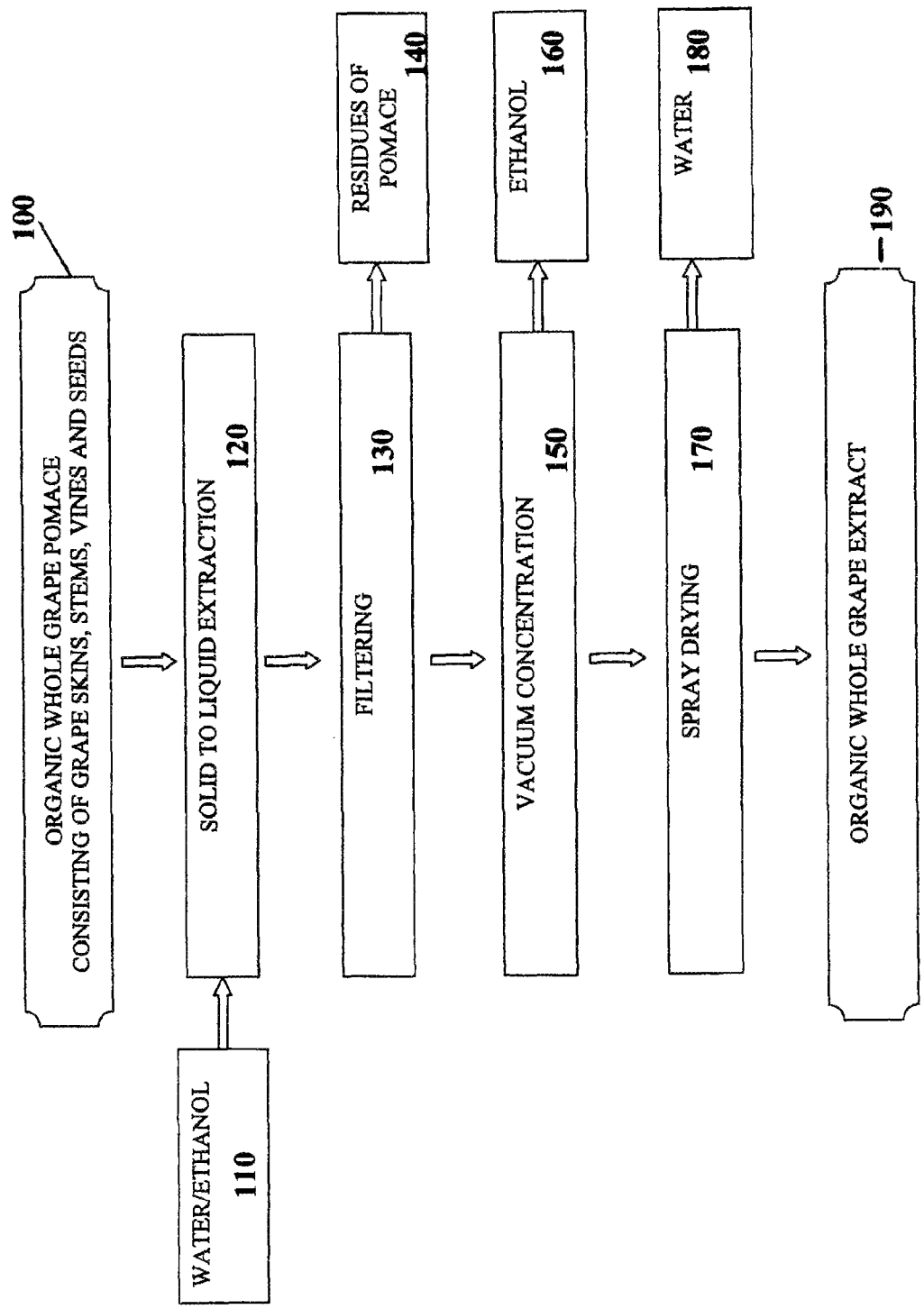
FIG. 2 is a flow chart of the process for preparing an organic whole grape extract in powdered form.

Another embodiment of the processing of whole grape pomace is shown in FIG. 2. Harvested or purchased grapes are processed to form a whole grape pomace 100 consisting of pomace, grape skins, stems, vines and seeds. Water/ethanol mixture 110 is used in a solid to liquid extraction step 120, the water, ethanol, solid mixture is then filtered 130 to remove the pomace residue 140. The remaining filtrate containing ethanol, water and grape solids is processed by vacuum concentration 150 to remove ethanol 160, the remaining concentrate is spray dried 170 to remove water 180 and the spray dried concentrate is collected and used as a organic whole grape extract 190. It should be noted that the residues of pomace 140, ethanol 160 removed by vacuum concentration, and water 180 removed during spray drying can be recycled for continuous use in the processing of whole grape pomace 100 to whole grape extract 190. The whole grape extract 190 is suitable for mixing with *polygonum cuspidatum* in the granulation process described herein and subsequently used to prepare dietary supplement capsules, liquids, tablets and the like.

The present invention is enhanced by the unique 'granulation' process which protects part of the total phytochemical blend from atmospheric conditions that include heat, air and humidity. The granulation process enhances stability by creating a cellulose barrier that protects the trans-resveratrol and other polyphenols from oxidative damage for an extended period of time. During the granulation process a bioflavanoid is mixed with the *polygonum cuspidatum* and organic pomace powder which allows for increased bioavailability of trans-resveratrol, and other naturally occurring polyphenols, to consumers.

The granulation process includes the use of a high density cellulose which protects the material from heat, humidity and UV light in atmospheric conditions and the addition of a bioflavanoid which produces a product that provides greater bioavailability of the trans-resveratrol and also a more stable trans-resveratrol. Thus, the present invention provides a significant improvement over the state of the art processes for preparing organic trans-resveratrol and dietary supplements therefrom.

A bioflavanoid, such as, quercetin dihydrate is added to the pomace powder during the granulation process. Animal testing proves that the added bioflavanoid enhances the absorption of the trans-resveratrol by the consumer. The granulated material is then dried at 26.6° C. (80 degrees Fahrenheit) until the moisture content is less than 1% by weight. After the material is dried, the material is stored in specialized polyurethane containers to protect the product from UV light exposure 24.

The manufacturing facility stores the material 25 in a cool, dark, dry location for placing into capsules or use in liquids, tablets, and the like. 26. The processed capsules, liquid, tablets, and the like are packaged in dark containers 27 to prevent exposure to UV light. The containers are shipped to the final destinations 28 in a controlled environment provided by the containers that are water and moisture resistant as well as being UV light resistant.

Experimentation has shown that use of specialized storage containers which limit UV light exposure and maintain humidity within a certain range or level also provides and enhances stable trans-resveratrol isomer yields. Research has shown that trans-resveratrol stored at a temperature range of 10.0° C. (50 degrees F.) to approximately 30° C. (86 degrees F), and at humidity levels of less than 35 percent causes the trans-resveratrol to remain stable during storage and processing.

The material is stored in specialized dark blue polyurethane drums designed to vacuum seal the material from humidity and moisture. The specialized dark blue polyurethane drums completely protect the material from UV light exposure. Dark blue polyurethane drums have been shown to shield UV light exposure at a much higher rate than all other polyurethane containers.

The present invention has created a Full Spectrum Resveratrol Polyphenol Blend that utilizes *polygonum cuspidatum*, grape vines, grape pomace from organically grown French and American Muscadine grapes as the sources for a diverse and unique resveratrol profile. Full Spectrum is used to describe the resveratrol polyphenol blend resulting from trans-resveratrol from multiple plant species, along with naturally occurring polyphenols such as catechin, epicatechin and OPCS (oligomeric proanthocyanidins) which enhances total trans-resveratrol benefits.

Examples 1-3 below provide processing conditions and details of the present invention beginning with the harvesting of grapes and pressing of grapes to form a pomace and a granulation process for preparation of a dietary supplement with a high organic trans-resveratrol content and high bioavailabity to the consumer.

Example 1

Harvesting Grapes, Vines and Leaves

In a grape vineyard located approximately five minutes from a processing facility, a worker manually cuts grape clusters from vines using a straight tip pruning shear. The grape clusters together with residual stems and leaves are placed in a canvas bag and within a time period of from approximately one to approximately twenty minutes, preferably 5 minutes, the cloth bag containing grape clusters, stems and leaves is delivered to a temperature controlled processing facility. The temperature within the facility is maintained in a range from approximately 21.1° C. (70 degrees F.) to approximately 29.4° C. (85 degrees F.), preferably at approximately 26.6° C. (80 degrees F.).

Example 2

Process for Obtaining Stable Organic Trans-Resveratrol

In a temperature controlled processing facility, wherein the temperature is approximately 26.6° C. (80 degrees F.), 100 kilograms of grapes, stems and leaves are removed from cloth bags; the grapes, vines and leaves are separated. The vines and leaves are stored for later use. The grapes are placed into a cylinder where they are compressed at high pressures, such as 80 pounds per square inch (psi). The pressing extracts grape juice which is subsequently used as a grape extract. The material left in the cylinder from the pressing of the grapes is a pomace of seeds, flesh and skin.

Twenty five (25) kilograms of pomace is removed from the cylinder and stored with vines and leave. The pomace, vines and leaves are packaged and taken to a temperature controlled extraction facility.

At the extraction facility, the pomace, vines and leaves are ground up into a fine powder which has a moisture content of approximately 1.0% by weight. The powder also has a mesh size in a range between approximately 40 mesh to approximately 80 mesh, preferably approximately 50 mesh. When the powder is analyzed for organic-trans resveratrol, the analysis shows approximately 97-99% trans-resveratrol to approximately 1-3% cis-resveratrol.

Twenty five (25) kilograms of fine powder consisting of pomace, vines and leaves is stored in a cool, dark, dry location for shipping to the dietary supplement manufacturing facility. The temperature range of the storage area is in a range of between approximately 10.0° C. (50 degrees F.) to approximately 30° C. (86 degrees F.) and the dry location has a humidity level of less than 35 percent water vapor in the air. With temperature and humidity controlled at the stated levels, the organic trans-resveratrol remains a stable compound in high yield.

Example 3

Process for Preparing Dietary Supplements

Fifty (50) kilograms of stable *polygonum cuspidatum* along with organic trans-resveratrol in the form of a fine powder in an approximately 50 mesh size is put in a granulator, and the granulation process includes the use of a high density cellulose coating which protects the material from heat, humidity and UV light in atmospheric conditions.

Two hundred (200) to five hundred (500) grams of a bioflavanoid is added to 10.0 kilograms of powdered *polygonum cuspidatum* along with organic trans-resveratrol during the granulation process, so that the mixture of bioflavanoid and *polygonum cuspidatum* along with organic trans-resveratrol powder is easily and readily absorbed by the consumer.

The mixture of bioflavanoid and *polygonum cuspidatum* along with organic trans-resveratrol powder is dried at approximately 26.6° C. (80° F.) to reduce the moisture content to a range between 0.1 weight % to approximately 10 wt. %, preferably 1.0 wt. %. After the material is dried, it is stored in dark blue polyurethane containers to protect the product from ultraviolet (UV) light exposure.

The temperature range of the storage area in the manufacturing facility is in a range of between approximately 10.0° C. (50 degrees F.) to approximately 30° C. (86 degrees F.) and the humidity of the storage area is less than 35%. Once processed dietary supplement capsules, liquid or tablets are then packaged in dark containers to prevent exposure to UV light.

The present invention has provided a high quality and high quantity of a stable, trans-resveratrol in a bioavailable, easily absorbable form for the consumer of the dietary supplements prepared therefrom. The quality of the *polygonum cuspidatum* and organic pomace is measured by low levels of impurities and low levels of microbial growth. The quantity of stable trans-resveratrol is measured against products that are commercially available. The high quantity of stable, trans-reveratrol delivered by the present invention is greater than 10% higher than commercially available trans-resveratrol products on the market in 2010.

Thus, trans-resveratrol, the sensitive and potent active antiinflammatory and antioxidant that helps cells regulate internal harmful mechanisms is available in a capsule, tablet or liquid thanks to the ingenuity of the invention disclosed herein.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method of processing trans-resveratrol for use in dietary supplements consisting essentially of the steps of:
    solely harvesting organically grown grapes, vines and leaves;
    placing the harvested organically grown grapes, the vines and the leaves in a cloth sack;
    transporting the harvested organically grown grapes and the vines to a separating location in a time period between approximately 4 minutes to approximately 25 minutes after harvesting;
    separating the organically grown grapes from the vines and the leaves;
    pressing the organically grown grapes until a pomace of grape skin, grape seeds and grape stems is left in a container;
    removing the pomace from the container;
    adding the vines and the leaves to the pomace;
    shipping the pomace to an extraction location with vines and leaves;
    storing the pomace, the vines and the leaves at the extraction location;
    grinding the pomace, the vines and the leaves into a fine powder;
    shipping the fine powder to manufacturing location;
    mixing the fine powder with bioflavanoid nutrients and *polygonum* into a mixture;
    processing the mixture in a granulator to form a granulated mixture;
    coating the granulated mixture with a cellulose barrier coating to protect the granulated mixture from heat, humidity and UV light in atmospheric conditions;
    storing the granulated mixture with the cellulose bather coating in a vacuum sealed UV light protected container;
    shipping the vacuum sealed container to the manufacturing location;
    preparing a dietary supplement product in the form of at least one of capsules, liquids and tablets from the granulated mixture with the cellulose bather coating;

placing prepared capsules, liquids and tablets into a closed container; and shipping the closed container to final destination, wherein the dietary supplements contains approximately 97 to 99 percent stable organic trans-resveratrol to approximately 1 to 3% cis-resveratrol with low levels of impurities and low levels of microbial grown.

2. The method of claim 1, wherein the organically grown grapes and the vines are selected from organically grown French Muscadine grapes, American Muscadine grapes and mixtures thereof.

3. The method of claim 1, wherein the transporting to a separating facility is a time period of from approximately five minutes to approximately ten minutes of harvesting.

4. The method of claim 1, wherein the pomace of grape skin, grape seeds and grape stems is mixed with the vines and the stems, and is ground to a fine powder, wherein the powder has a mesh size in a range between approximately 40 mesh to approximately 80 mesh.

5. The method of claim 1, wherein the fine powder is mixed with the bioflavanoid nutrients into a compound, the bioflavanoid nutrients is selected from at least one of quercetin dihydrate, hesperidin complex, and rose hips concentrate.

6. The method of claim 5, wherein the bioflavanoid compound is quercetin dihydrate.

7. The method of claim 1, wherein the controlled environment for storage of the fine powder and bioflavanoid mixture includes a temperature range of between 10.0° C. (50 degrees F.) to approximately 30° C. (86 degrees F.) and a humidity level in the storage area of less than 35% water vapor in the air.

8. The method of claim 1, wherein the granulated mixture is dried at approximately 26.6° C. (80° F.) to reduce the moisture content of the mixture to a range between 0.1 weight % to approximately 10 wt. %.

9. The method of claim 8, wherein the moisture content of the granulated mixture is approximately 1% by weight.

10. The method of claim 9 further consisting of the step of preparing dietary supplements in the form of at least one of capsules, liquids and tablets.

11. The method of claim 10, wherein the shipping step includes storing the capsules, liquids and tablets in dark containers for shipment.

12. A method of processing trans-resveratrol for use in dietary supplements consisting of the steps of:

solely harvesting organically grown grapes, vines and leaves;

separating the organically grown grapes from the vines and the leaves;

pressing the organically grown grapes until a pomace of grape skin, seeds and stems is left;

adding the vines and the leaves to the pomace;

grinding the pomace, the vines and the leaves into a fine powder;

mixing the powder with bioflavanoid nutrients and *polygonum* into a mixture;

processing the mixture in a granulator to form a granulated mixture;

coating the granulated mixture with a cellulose barrier coating to protect the granulated mixture from heat, humidity and UV light in atmospheric conditions; and preparing a dietary supplement product in the form of at least one of capsules, liquids and tablets from the granulated mixture with the cellulose barrier coating, wherein the dietary supplements contains approximately 97 to 99 percent stable organic trans-resveratrol to approximately 1 to 3% cis-resveratrol with low levels of impurities and low levels of microbial grown.

\* \* \* \* \*